(12) United States Patent
McCall

(10) Patent No.: US 7,641,612 B1
(45) Date of Patent: Jan. 5, 2010

(54) BLOOD LOSS DETECTION FOR HEMODIALYSIS SYSTEM

(76) Inventor: Kenneth Shawn McCall, 313 N. Cedar, Owasso, OK (US) 74055

( * ) Notice: Subject to any disclaimer, the term of this patent is extended or adjusted under 35 U.S.C. 154(b) by 305 days.

(21) Appl. No.: 11/306,947

(22) Filed: Jan. 17, 2006

(51) Int. Cl.
  *A61B 5/0265* (2006.01)
  *A61B 5/00* (2006.01)
  *A61M 5/00* (2006.01)

(52) U.S. Cl. ........... 600/371; 210/739; 210/645; 210/646; 210/649; 210/650; 210/651; 600/362

(58) Field of Classification Search ......... 210/645–646, 210/600, 634, 649–651, 739–741, 744–745, 210/767, 194, 195.1, 195.2, 252, 257.1, 572.2; 422/44–48; 604/1–11; 600/371, 362
See application file for complete search history.

(56) References Cited

U.S. PATENT DOCUMENTS

| 6,752,785 | B2 | 6/2004 | Van Antwerp et al. | 604/111 |
| 2005/0010265 | A1* | 1/2005 | Baru Fassio et al. | 607/48 |
| 2005/0038325 | A1* | 2/2005 | Moll | 600/300 |
| 2007/0293748 | A1* | 12/2007 | Engvall et al. | 600/371 |

FOREIGN PATENT DOCUMENTS

| WO | WO 99/24145 | * | 5/1999 | 200/127 |
| WO | WO/99/24145 | * | 5/1999 | 200/127 |
| WO | WO/2006/001759 | * | 1/2006 | 600/526 |

OTHER PUBLICATIONS

Redsense Medical (description of the sensor device) [online] Retrieved Feb. 6, 2009 from the Internet <URL:http://www.redsensemedical.com/Pages/Default.aspx?PageID=2>.*

Redsense Medical User Manual—English (Jun. 28, 2008), Retrieved Feb. 6, 2009 from the Internet <URL:http://www.redsensemedical.com/Pages/ListPressItems.aspx>.*

"Catastrophic Hemorrhage from Venous Needle Dislodgement During Hemodialysis: Continued Risk of Avoidable Death and Progress Toward a Solution"; Stephen Sandroni; American Society of Nephrology Renal Week 2008 (publications), p. 891A-892A; PUB354.

(Continued)

*Primary Examiner*—Krishnan S Menon
*Assistant Examiner*—Marjorie Christian
(74) *Attorney, Agent, or Firm*—Head, Johnson & Kachigian, PC

(57) ABSTRACT

A blood loss detection device for a hemodialysis system having a blood intake line, a dialysis machine including a pump, with the dialysis machine in communication with the blood intake line, and a blood return line in communication with the dialysis machine. The detection device includes a patch having an exterior edge and an opening through the patch forming a target for receipt of the return blood line. A slit through the patch extends between the exterior edge and the opening. A primary loop circuit terminates at two ends at the slit. An early warning alarm circuit loop terminates at two ends at the slit. An emergency shut-down circuit loop terminates at two ends at the slit. A modular connector connects the patch to an alarm activated by the early warning alarm circuit and to a switch mechanism activated by the shut-down circuit in order to shut down the dialysis machine and the pump.

7 Claims, 5 Drawing Sheets

OTHER PUBLICATIONS

"New Estimates of Fatal Incidents"; Redsense Medical AB, http://www.redsensemedical.com/Pages/ShowNews.aspx?NewsID=62.

"Potential Benefits and Risks of Hemodialysis"; Your Total Health; http://yourtotalhealth.ivillage.com/hemodialysis.html?pageNum=5.

"Keep An Eye on Your Needle", Jane Hurst, RN, KidneyTimes, http://www.kidneytimes.com/article.php?id=20081217152602.

"What Kind of Infections Can Occur in Hemodialysis Patients?", AAKP, http://www.aakp.org/aakp-library/infections-in-hemodialysis-patients/.

Dr. Robert A. Mactier and Dr. David P. Worth, "Minimizing the Risk of Venous Needle Dislodgement During Hemodialysis".

Discussion of Venous Needle Dislodgement During Hemodialysis: An Unresolved Risk of Catastrophic Hemorrhage:, Dr. Stephen Sandroni (Hemodialysis International, Jan. 2005; 9:102), European Dialysis & Transplant Nurses Association European Renal Care Association; http:/www.edtnaerca.org/pages/education/journalclub/summary2005_2.php.

"Venous Needle Dislodgement: How to Mnimise the Risks", Jean-Pierre Van Waeleghem et al.; Journal of Renal Care 2008, p. 163-168.

"Recommendations for Preventing Transmission of Infections Among Chronic Hemodialysis Patients", MMWR, Apr. 27, 2001/SO(RROS); 1-43; http://www.cdc.gov/MMWR/preview/mmwrhtml/rr5005a1.htm.

"Venous Needle Dislodgement (VND), How to Minimize the Risks", EDTNA/ERCA Recommendations for Renal Nurses.

* cited by examiner

BLOOD LOSS DETECTION FOR HEMODIALYSIS SYSTEM

BACKGROUND OF THE INVENTION

1. Field of the Invention

The present invention relates to a blood loss detection device and method for a hemodialysis system.

2. Prior Art

Hemodialysis is a known medical procedure through which a person's blood is cleansed of toxins. Hemodialysis is often prescribed when the kidneys no longer function properly for any of a number of reasons. Hemodialysis is typically performed at a hospital or dialysis center although there is interest in and a trend toward home use. In a dialysis treatment, the patient is connected to a hemodialysis machine via two tubes. The first tube is a blood intake tube and is responsible for removing blood from the patient and transferring it to the machine. When the blood enters the machine, it is cleaned via semi-permeable filters and then is pumped back to the patient through a blood return tubing. Before hemodialysis can be done, a doctor must make an entrance, often called an "access", into the patient's blood vessels. This is sometimes done by minor surgery in the leg, arm or neck. The best access for many patients is called a "fistula". Minor surgery may be performed to join an artery to a vein under the skin to make a larger vessel.

The dialysis process can take several hours for each procedure and may be done more than once per week depending on the condition. Even if done in the supervision of medical professionals, a patient cannot be monitored every minute. Additionally, a blanket or blankets will often be placed on the patient and the patient may attempt to nap or sleep during the procedure.

There have been reports of the return line becoming accidentally dislodged or pulled from the access site in the patient. If the dialysis machine and its accompanying pump continue to operate, blood will be drawn from the patient but will not properly be returned to the patient. If this condition continues, the patient can suffer loss of blood and even death. While the hemodialysis machines have existing pressure sensing devices, they may not sense the condition if the blood continues to pump. Additionally, if the patient is sleeping or if medical personnel are not constantly observing the entire procedure, blood loss may occur until it is discovered.

Several prior attempts have been made relating to various leak detection systems. For example, Van Antwerp et al. (U.S. Pat. No. 6,752,785) shows a wide variety of leak detection devices including devices as shown in FIGS. 10(a), 10(b) and 10(c). Each of these devices must be applied to the body of a user before a needle is inserted since each includes an enclosed circular opening. The Van Antwerp devices can not be installed once the return line is attached to the patient. If the Van Antwerp device was placed on the patient first, it would involve breaking the sterile field which is created and normally desirable on the skin of the patient before insertion of the needle. If the Van Antwerp device were to be placed prior to inserting the needle into the patient, the sterile field of the access site would be compromised, possibly resulting in an infection of the patient's blood.

Accordingly, it would be desirable to provide for protection of hemodialysis patients from exsanguination.

It would be desirable to provide a blood loss detection device and method which might be installed around a return line or needle connected to the patient.

It would also be desirable to provide a blood loss detection device and method which is simple and modular in design which could be easily placed or replaced without interruption of treatment.

It would further be desirable to provide a blood loss detection device and method which has both an alarm and a shut-down system which operates in conjunction with or separately from existing hemodialysis systems.

It would further be desirable to provide a blood loss detection device and method having a modular connection with a sensor system to confirm the modular connection.

SUMMARY OF THE INVENTION

The present invention provides a blood loss detection device and process which is utilized with and operates along with a hemodialysis system.

The detection device of the present invention includes a patch having a boundary or external edge extending around and circumnavigating the entire patch. The patch and its boundary edge may take many configurations including, but not limited to, a rectangle or circle.

The patch also includes a central opening through the patch which forms a target for receipt of the return access site and return blood line from the hemodialysis machine.

In at least one location there shall be an opening or slit from internal to external boundary edge to allow post access placement. Accordingly, the patch forms an enclosure and surrounds the return access site with the exception of the slit.

A primary loop circuit extends through a multi-conductor cable to the patch and terminates a pair of opposed ends at the slit in the patch. The multi-conductor cable carries the primary loop circuit to a source of voltage. The voltage power supply is, in turn, wired to an audio alarm. Accordingly, the primary loop circuit delivers and provides operational voltage/signal. An early warning alarm loop circuit passes from the multi-conductor cable into the patch and terminates at two ends at the slit. The early warning alarm loop circuit passes from the patch, through the multi-conductor cable, and back to the audio alarm.

An emergency shut-down circuit loop extends from the multi-conductor cable into the patch and terminates at two ends at the slit. The emergency shut-down circuit loop extends from the multi-conductor cable to the dialysis machine and, in particular, to the blood pump.

The present invention is also modular in design so that the device may be quickly installed, quickly removed, and replaced as desired. The multi-conductor cable extends from the patch and terminates in a male modular connector which cooperates with a female modular connector which is, in turn, connected to a multi-conductor cable from the hemodialysis machine and the component elements thereof.

The invention is designed to detect blood loss associated with the blood return system of hemodialysis.

The invention is a boundary designed to encircle the access site of the blood return system of hemodialysis. The boundary will have an adhesive backing to maintain proper placement of the detection device during use.

The inner and outer boundaries of the detection device will enclose one or more open electrical circuits. These circuits will be composed of one primary input conductor and any number of secondary conductors returning to the hemodialysis machine.

The hemodialysis machine will monitor the return conductors and as long as the status of the conductors remains unchanged, the treatment will proceed. If at some point the machine should detect a status change across any return conductor, it would initiate a proper response to input information. This status change could be a detectable change in the existing physical properties of the conductors such as input voltage or impedance/resistance on existing circuit.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's shape, construction and the arrangement of its components without departing from the spirit and scope of this disclosure. It is understood that the invention is not limited to the embodiments set forth herein for purposes of exemplification.

Figure 1:
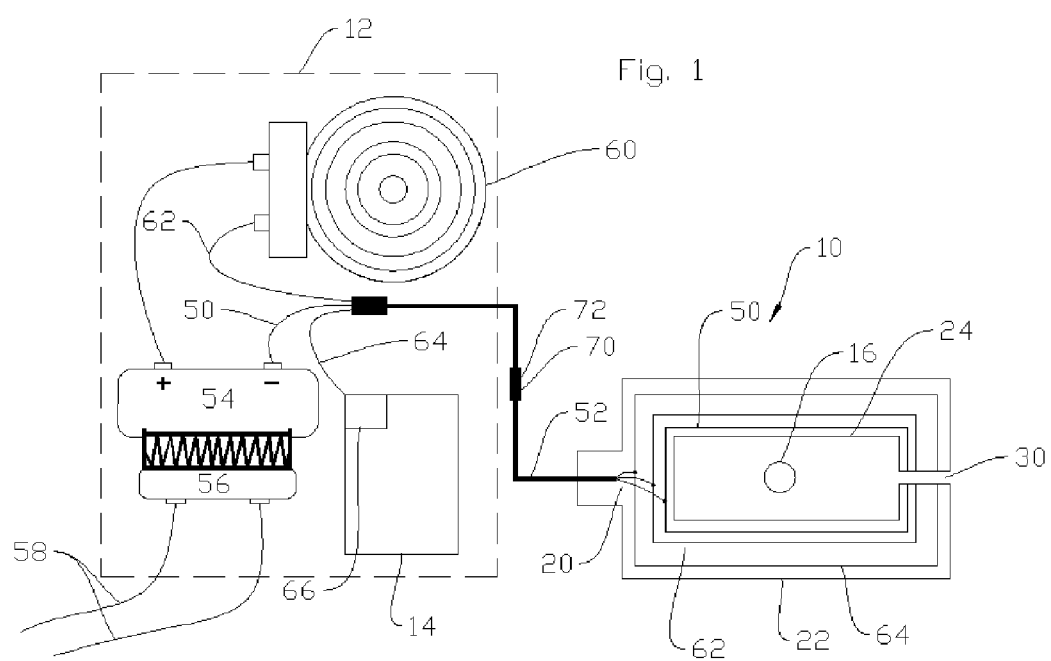
FIG. 1 is a simple diagrammatic view of a blood loss detection device constructed in accordance with the present invention in communication with a hemodialysis system.

Referring to the drawings in detail, FIG. 1 illustrates a simple diagrammatic view of a blood loss detection device 10 constructed in accordance with the present invention.

The blood loss detection device 10 is utilized with and operates along with a hemodialysis system, represented by dashed lines 12.

Hemodialysis machines and the hemodialysis procedure are both well-known. A patient (not shown) will have a fluid intake tube connected through an access into the blood vessels of the patient. The blood is pumped via a pump (shown diagrammatically by box 14) into and through the hemodialysis machine 12 where the blood is cleansed. The blood is thereafter returned via a blood return line to the patient through a return access site 16.

The detection device 10 of the present invention includes a patch 20 having a boundary or external edge 22 extending around and circumnavigating the entire patch. The patch 20 and its boundary edge 22 may take many configurations including, as shown in FIG. 1, a substantially rectangular form.

The patch 20 also includes an opening 24 through the patch which forms a target for receipt of the return access site 16 and the return blood line (not shown) from the hemodialysis machine 12.

A slit 30 through the patch 20 extends from the boundary edge 22 to the patch opening 24. Accordingly, the patch forms an enclosure and surrounds the return access site 16 with the exception of the slit 30. The ends may be overlapped to form a complete enclosure.

The blood access site monitor consists of a base with adhesive backing, would be able to substantially encircle the blood access site and within its inner and outer boundaries contain the primary input circuit and required number of monitoring circuits. The access site monitoring device or patch should be composed of a permeable material that would facilitate transfer of any blood loss across the primary input conductors.

Figure 2:
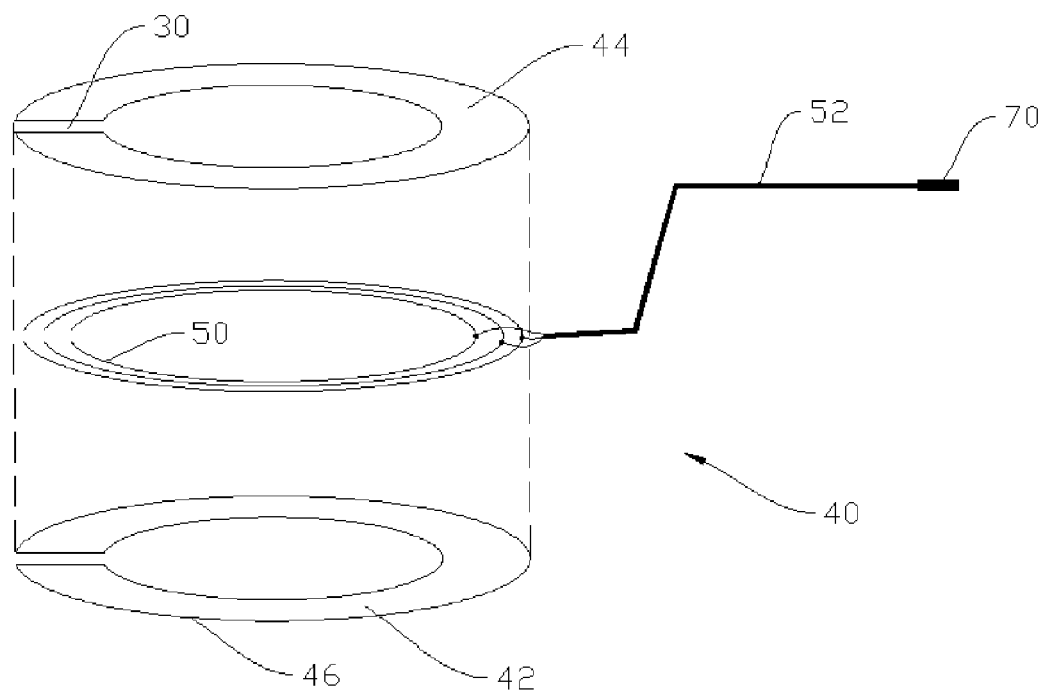
FIG. 2 illustrates an exploded view and FIG. 3 illustrates a top view of an alternate embodiment of the detection device of the present invention.
Figure 3:
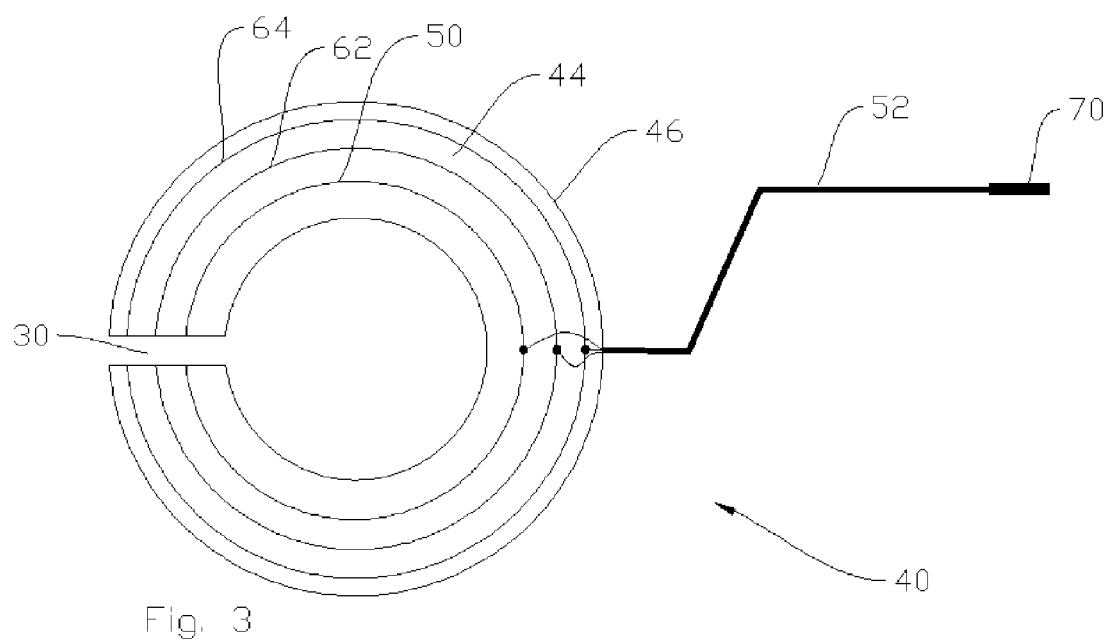

FIGS. 2 and 3 illustrate an alternate embodiment of the detection device 10. FIG. 2 shows an exploded view of an alternate embodiment 40 while FIG. 3 illustrates a top view. The patch 40 includes a first layer 42 having an adhesive base designed to adhere to a skin of a patient. Above the first layer 42 are the electrical conductors to be described. A top layer 44 covers both the electrical conductors and the first layer 42. The boundary edge 46 of the alternate embodiment 40 is in the form of a circle.

Finally, an optional transparent cover (not shown) could be adhesively secured to the top layer 44. The cover might be transparent to allow for visual observation but retain any blood loss.

With reference to FIG. 1 and continuing reference to FIGS. 2 and 3, a primary input conductor loop 50 extends through a multi-conductor cable 52 via a primary loop conductor to the patch (reference numeral 10 in FIG. 1 and reference numeral 40 in FIGS. 2 and 3). The primary input conductor loop 50 terminates at a pair of opposed ends at the slit 30 in the patch. The multi-conductor cable 52 carries the primary loop circuit conductor to a DC voltage power supply 54 which, in turn, is connected to transformer 56 and thereafter connected to alternating current power supply 58. The power supply is, in turn, wired to an audio alarm 60. Accordingly, the primary input conductor loop 50 delivers and provides operational voltage to the detection device 10.

An early warning alarm loop circuit 62 passes from the multi-conductor cable 52 into the patch 20. The early warning alarm loop circuit 62 terminates at two ends at the slit 30. The early warning alarm loop circuit 62 passes from the patch 20 through the multi-conductor cable 52 and back to the audio alarm 60.

An emergency shut-down circuit loop 64 extends from the multi-conductor cable 52 to the patch 20. The emergency shut-down circuit loop 64 terminates at two ends at the slit 30.

The emergency shutdown circuit loop 64 extends through the multi-conductor cable 52 via the emergency shutdown circuit loop conductor to the dialysis machine 12 and, in particular, to the pump 14. The emergency shut-down circuit loop 64 includes a switch mechanism 66 to shut down the dialysis machine 12 and, in particular, the pump 14.

The present invention is modular in design so that the blood loss detection device 10 may be quickly installed, removed and replaced as desirable.

The multi-conductor cable 52 extending from the patch 40 terminates in a male modular connector 70. The male modular connector 70 will cooperate with a female modular connector 72 connected to multi-conductor cable 52 which, in turn, is connected to the hemodialysis machine 12 and the component elements previously discussed.

Figure 4:
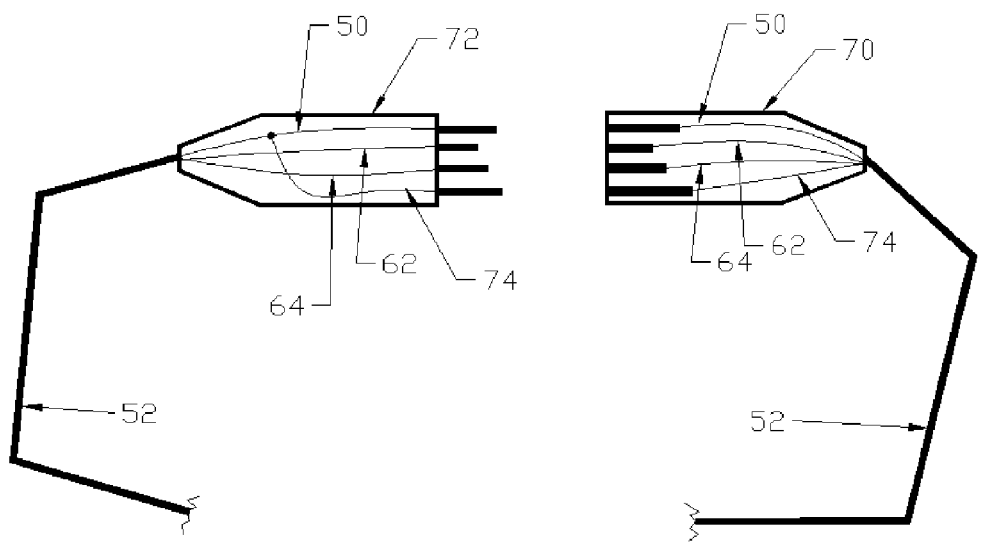
FIG. 4 is a simple illustration of the modular connectors of the present invention.

FIG. 4 illustrates the modular connectors with an optional feature of an optional safety electric loop circuit. In addition to the primary loop circuit 50, the early warning alarm circuit 62 and the emergency shut-down circuit 64, the modular connectors include an optional safety loop circuit 74.

Figure 5:
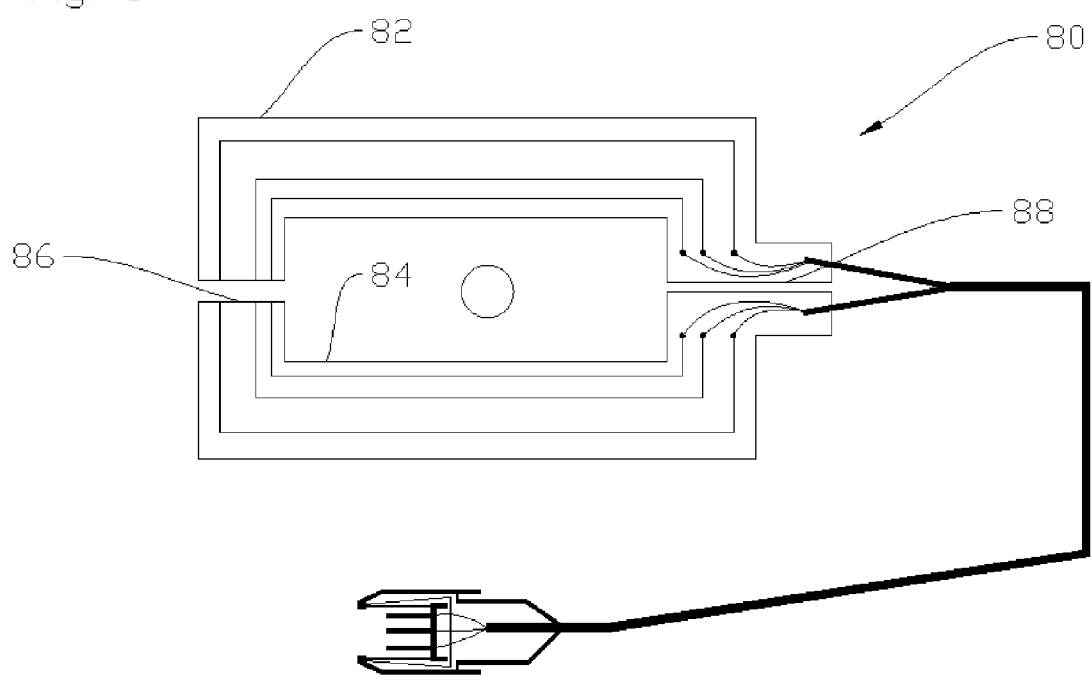
FIG. 5 illustrates a further alternate embodiment of a blood loss detection device (double split design) constructed in accordance with the present invention.
Figure 6:
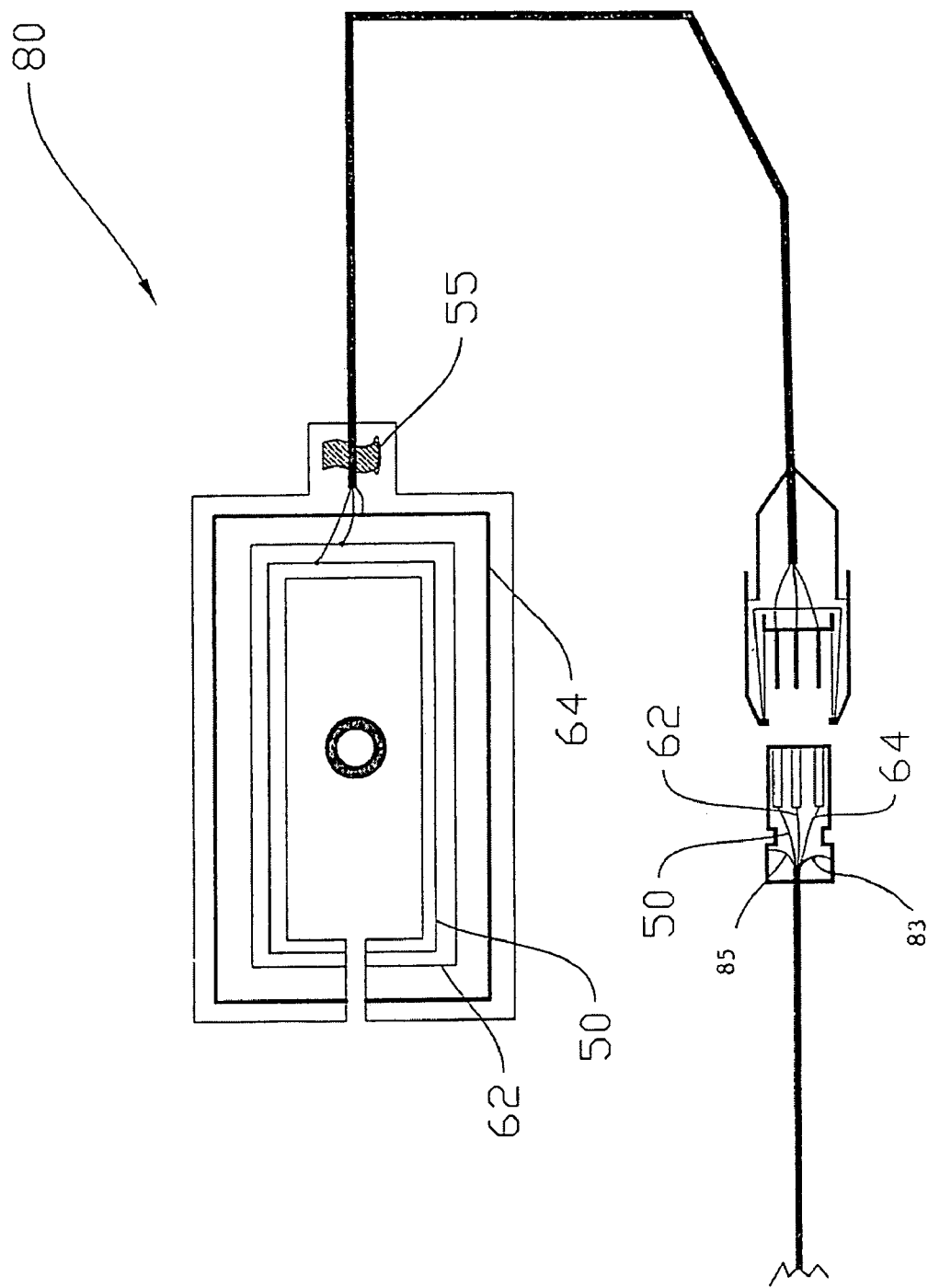
FIG. 6 illustrates a further alternate embodiment of a blood loss detection device with a self-monitoring plug.

FIGS. 5 and 6 show another embodiment of a safety loop modular connector. FIG. 5 shows a further alternate embodiment of the present invention including a patch 80 having a boundary edge 82 and an opening 84. Slits 86 and 88 extend through patch 80 between the boundary edge 82 and the opening 84.

Finally, FIG. 5 illustrates a further alternate embodiment 80 of the invention utilizing a double split in the patch and a modular self-monitoring plug.

For simple description of operation in FIG. 1, the illustrations will be limited to one input conductor and two return or output circuits. In the illustration, the inner 24 and outer 22 boundaries enclose three conductors—the primary input conductor loop circuit 50, an early alarm circuit loop 62 and an emergency shut-down conductor loop 64.

As long as the dialysis machine does not sense a change or input voltage on conductor 62 or 64, the treatment would proceed without interruption. If the machine detects a change in the status of conductor 62, it would activate some type of notification alarm and staff could address the problem and treatment would continue uninterrupted. If at any point during treatment, the machine would detect a change in the status of conductor 64, the machine would initiate an alarm and shut down the blood pump, preventing blood flow to the blood return access site.

The device shown in FIG. 6 also includes a tubing clip 55 to retain the needle and fluid tube (not shown) in association with the patch.

A machine connection lead is composed of a multi-conductor cable that originates from control connections within the machine and terminates at a modular female connector. The number of conductors is variable and will depend on the monitoring configuration of the patch or access monitoring device. In the most basic design there would be at least two conductors, the first conductor would provide signal input to the monitoring device or patch and the second would provide a return path or output to the dialysis machine should a blood loss incident occur. In more advanced designs there would be additional conductors that would communicate other features/embodiments back to the machine for monitoring. In the embodiment disclosed, the machine connection lead would contain four to five conductors. The first conductor loop 50 would be the signal loop input conductor or what is referred to as line voltage. The second conductor loop 62 would be part of an early warning circuit that would be activated by a small blood leak. The third conductor loop 64 would be part of an emergency shut-down circuit that would only be activated when a larger blood loss occurs. The fourth conductor loop 83 and fifth conductor loop 85 would be utilized in verifying that the modular connectors were properly connected.

As may be appreciated from the foregoing, the present invention may include optional circuits beyond the primary conductor and alarm/shut-down circuits set forth herein.

Whereas, the present invention has been described in relation to the drawings attached hereto, it should be understood that other and further modifications, apart from those shown or suggested herein, may be made within the spirit and scope of this invention.

What is claimed is:

1. A blood loss detection device for a hemodialysis system having a blood intake line, a dialysis machine including a pump, said dialysis machine in communication with said blood intake line, and a blood return line in communication with said dialysis machine, which detection device comprises:
   a patch having an external boundary edge circumnavigating said patch;
   a central opening through said patch so that said patch surrounds said central opening, wherein said central opening is within said boundary edge and forms a target for receipt of a return access site and said blood return line so that said opening of said patch surrounds and encloses said target;
   a slit through said patch extending between said boundary edge and said central opening;
   a primary circuit loop circumnavigating said central opening terminating at two ends at said slit;
   an early warning alarm circuit loop circumnavigating said central opening terminating at two ends at said slit;
   an emergency shut-down circuit loop circumnavigating said central opening terminating at two ends at said slit, said emergency shut-down circuit loop independent from said early warning alarm circuit loop wherein said primary circuit loop, said early warning alarm circuit loop, and said emergency shut-down circuit loop are in a radial plane; and
   a modular connector connecting said patch to an alarm activated by said early warning alarm circuit loop and to a switch mechanism actuated by said emergency shut-down circuit loop to shut down said dialysis machine and pump wherein said early warning alarm circuit loop is activated by a small blood leak and wherein said emergency shut-down circuit loop is activated by a larger blood loss.

2. A blood loss detection device as set forth in claim 1 wherein said modular connector includes a male connector and a female connector and an optional safety loop circuit to sense when said male and female connectors are joined.

3. A blood loss detection device as set forth in claim 1 wherein said emergency shut-down circuit is connected to said dialysis machine including said pump.

4. A blood loss detection device as set forth in claim 1 wherein said patch includes an adhesive base for connection to the skin of a patient.

5. A blood loss detection device as set forth in claim 4 wherein said patch includes a top layer.

6. A blood loss detection device as set forth in claim 1 wherein said patch boundary edge is any geometric shape that surrounds and forms an enclosure of the access site.

7. A method of blood loss detection for a hemodialysis system having a blood intake line, a dialysis machine including a pump, said dialysis machine in communication with said blood intake line, and a blood return line in communication with said dialysis machine, which method comprises:
   placing a patch having an external boundary edge circumnavigating said patch and a central opening through said patch forming a target for a blood return access site so that said patch surrounds said central opening;
   terminating a primary circuit loop at two ends at a slit extending between said external boundary edge and said central opening, terminating an early warning alarm circuit loop at two ends at said slit, and terminating an emergency shut-down circuit loop at said two ends of said slit, wherein said primary circuit loop, said early warning alarm circuit loop and said emergency shut-down circuit loop are in a radial plane and each circumnavigate said central opening;
   adhesively securing said patch to a patient;
   sensing a status change in properties when blood closes said primary circuit loop and said early warning alarm circuit loop and thereafter activating an alarm;
   sensing a status change in properties when blood closes said primary circuit loop and said emergency shut-down circuit loop; and
   thereafter shutting down said dialysis machine and said pump wherein said early warning alarm circuit loop and said emergency shut-down circuit loop operate independently.

* * * * *